(12) United States Patent
Barrus

(10) Patent No.: US 9,801,662 B2
(45) Date of Patent: Oct. 31, 2017

(54) SPINAL STABILIZATION SYSTEM

(71) Applicant: K2M, Inc., Leesburg, VA (US)

(72) Inventor: Michael Barrus, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 809 days.

(21) Appl. No.: 13/675,100

(22) Filed: Nov. 13, 2012

(65) Prior Publication Data

US 2014/0135843 A1    May 15, 2014

(51) Int. Cl.
    *A61B 17/70* (2006.01)
    *A61B 17/88* (2006.01)

(52) U.S. Cl.
    CPC ........ *A61B 17/701* (2013.01); *A61B 17/8863* (2013.01); *A61B 17/7032* (2013.01)

(58) Field of Classification Search
    CPC ...................................... A61B 17/70–17/7046
    USPC ........................................ 606/246, 254–279
    See application file for complete search history.

(56) References Cited

U.S. PATENT DOCUMENTS

| | | |
|---|---|---|
| 5,217,497 A | 6/1993 | Mehdian |
| 5,261,912 A | 11/1993 | Frigg |
| 5,658,286 A | 8/1997 | Sava |
| 5,667,508 A | 9/1997 | Errico et al. |
| 5,899,904 A | 5/1999 | Errico et al. |
| 5,910,142 A | 6/1999 | Tatar |
| 5,947,969 A | 9/1999 | Errico et al. |
| 5,989,250 A * | 11/1999 | Wagner et al. ............. 606/250 |
| 6,102,912 A | 8/2000 | Cazin et al. |
| 6,451,021 B1 | 9/2002 | Ralph et al. |
| 6,482,207 B1 | 11/2002 | Errico |
| 6,540,749 B2 | 4/2003 | Schafer et al. |
| 6,582,434 B2 | 6/2003 | Kawakami et al. |
| 6,595,992 B1 * | 7/2003 | Wagner et al. ............. 606/250 |
| 6,644,087 B1 | 11/2003 | Ralph et al. |
| 7,503,918 B2 | 3/2009 | Baccelli et al. |
| 7,520,879 B2 | 4/2009 | Justis et al. |
| 7,563,274 B2 * | 7/2009 | Justis et al. ................ 606/279 |
| 7,569,061 B2 | 8/2009 | Colleran |
| 7,588,575 B2 | 9/2009 | Colleran et al. |
| 7,588,588 B2 | 9/2009 | Spitler et al. |
| 7,604,653 B2 * | 10/2009 | Kitchen ....................... 606/257 |
| 7,618,442 B2 | 11/2009 | Spitler et al. |
| 7,766,942 B2 * | 8/2010 | Patterson et al. ............ 606/261 |
| 7,931,676 B2 | 4/2011 | Veldman et al. |
| 2002/0161368 A1 | 10/2002 | Foley et al. |
| 2005/0065515 A1 | 3/2005 | Jahng |

(Continued)

*Primary Examiner* — Jan Christopher Merene
*Assistant Examiner* — Steven Cotroneo
(74) *Attorney, Agent, or Firm* — Carter, DeLuca, Farrell & Schmidt, LLP

(57) ABSTRACT

A spinal stabilization system includes a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a set screw configured to secure the connecting rod in the slot. The slot includes a leading end portion configured to receive the elongate rounded section of the connecting rod and a trailing end portion configured to threadably engage the set screw, wherein the slot is flared such that elongate rounded section of the connecting rod is pivotable about the leading end portion of the slot.

10 Claims, 7 Drawing Sheets

(56) References Cited

U.S. PATENT DOCUMENTS

| | | |
|---|---|---|
| 2005/0273099 A1* | 12/2005 | Baccelli et al. ................ 606/61 |
| 2008/0086130 A1* | 4/2008 | Lake et al. ..................... 606/61 |
| 2009/0018593 A1 | 1/2009 | Barrus et al. |
| 2009/0088800 A1* | 4/2009 | Blain et al. ................... 606/246 |
| 2009/0198279 A1* | 8/2009 | Zhang et al. ................. 606/264 |
| 2010/0063544 A1* | 3/2010 | Butler .......................... 606/261 |
| 2011/0087298 A1 | 4/2011 | Jones |
| 2011/0190823 A1* | 8/2011 | Bergeron et al. ............ 606/264 |

\* cited by examiner

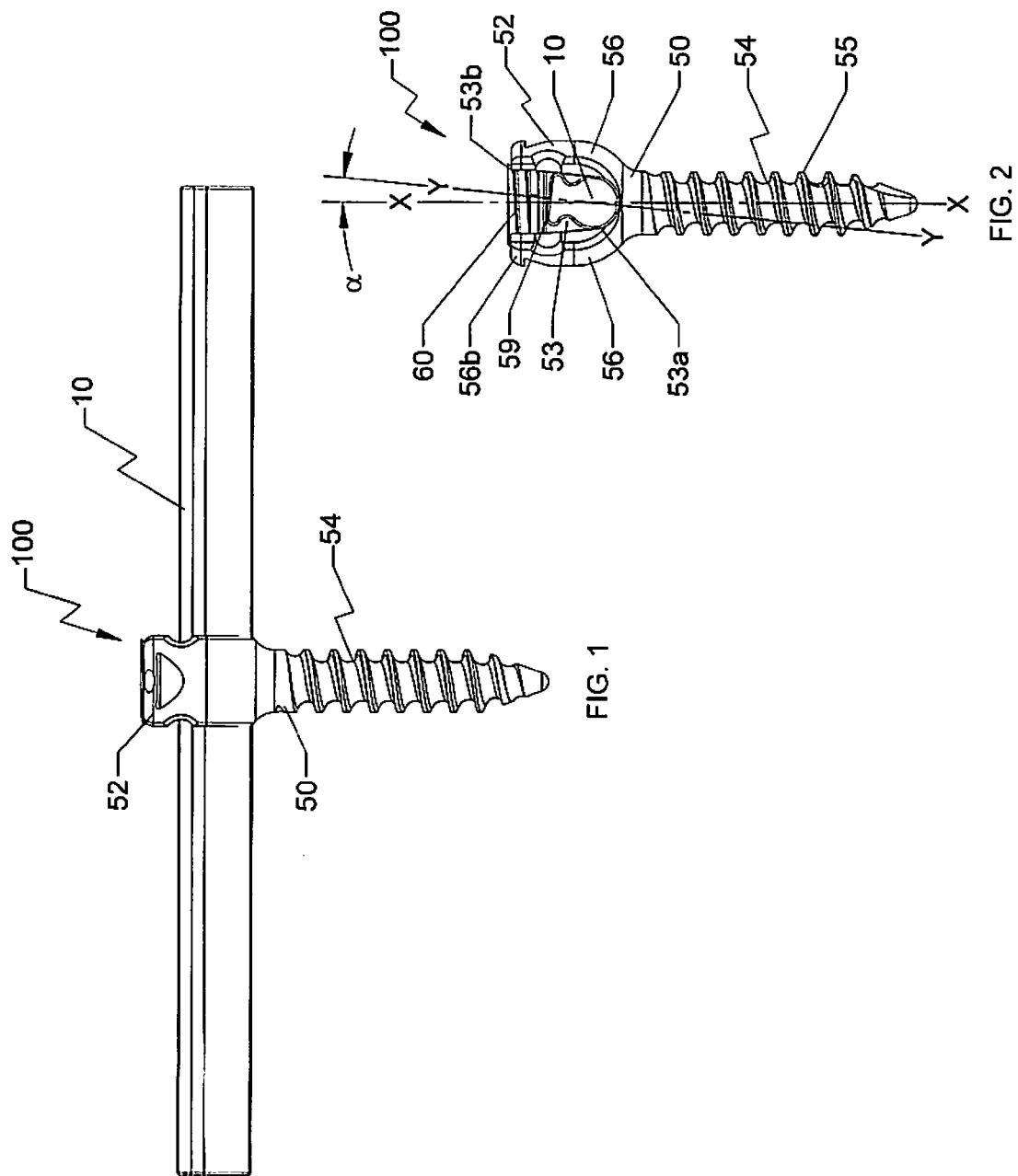

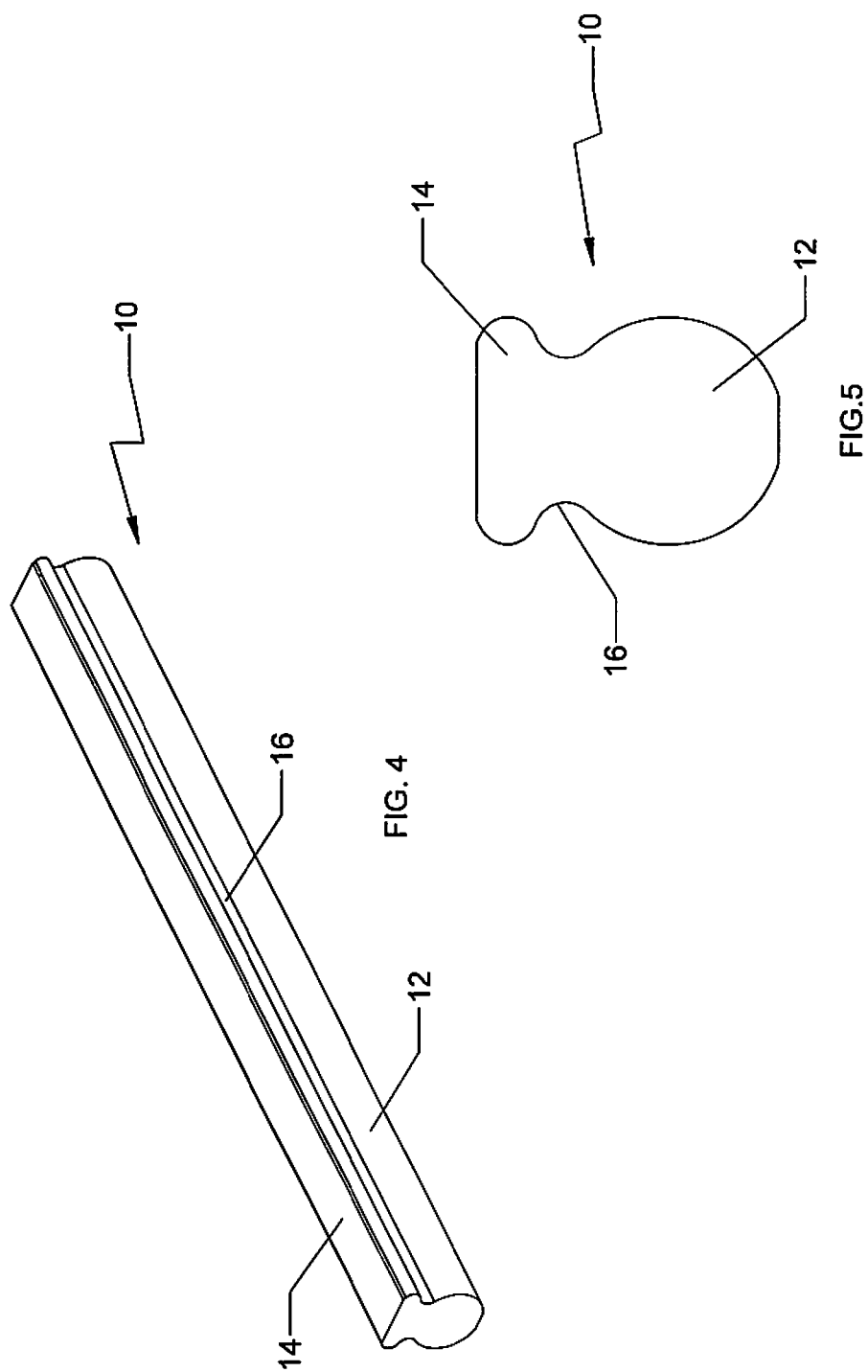

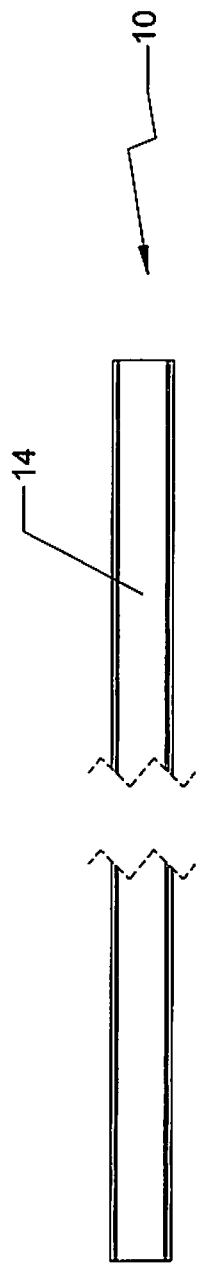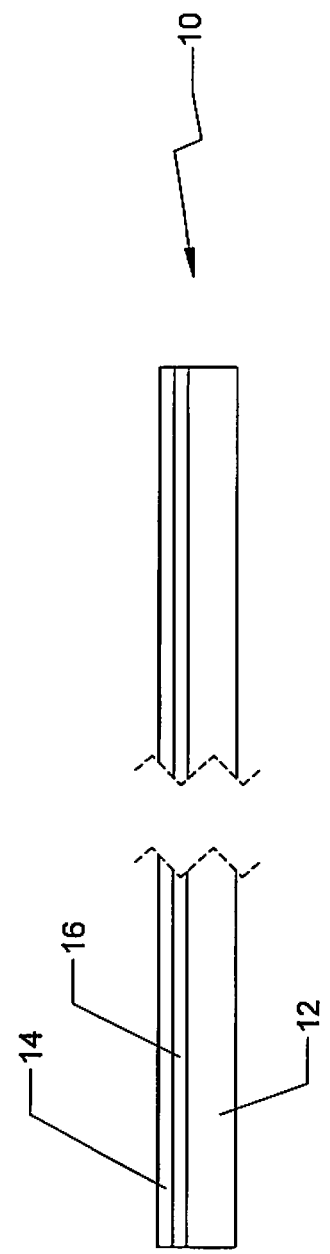

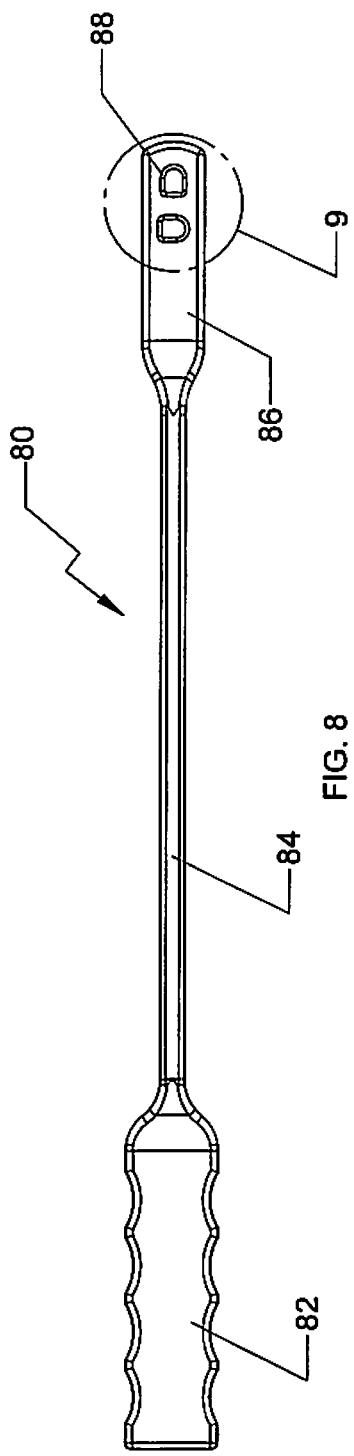
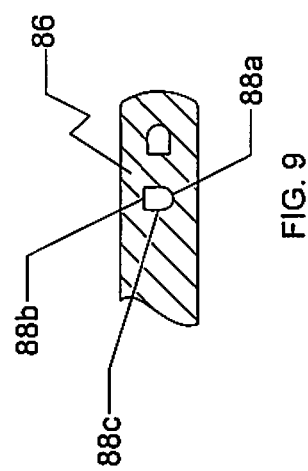
FIG. 8
FIG. 9

SPINAL STABILIZATION SYSTEM

BACKGROUND

Technical Field

The present disclosure relates to orthopedic surgical devices and, more particularly, to a spinal stabilization system.

Background of Related Art

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae, and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surf ice with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and connecting rods.

Often times, the surgeon needs to make adjustments to the orientation and/or position of the connecting rod relative to the bone screw. Therefore, a need exists for a simple and effective screw and rod construct that enables surgeons to easily and safely manipulate the connecting rod relative to the bone screws during a surgical procedure.

SUMMARY

In accordance with an embodiment of the present disclosure, there is provided a spinal stabilization system including a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a set screw configured to secure the connecting rod in the slot. The slot includes a leading end portion configured to receive the elongate rounded section of the connecting rod and a trailing end portion configured to threadably engage the set screw, wherein the slot is flared such that elongate rounded section of the connecting rod is pivotable about the leading end portion of the slot.

In an embodiment, the radius of the trailing end portion of the slot may be larger than that of the leading end portion of the slot. The leading end portion of the slot may have an arcuate configuration dimensioned to accommodate a circular cross-section of the elongate rounded section of the connecting rod.

In another embodiment, the head portion of the bone screw may include a pair of radially opposing walls defining the slot therebetween. In particular, the elongate head portion of the connecting rod may be movable toward and away from the pair of radially opposing walls of the slot.

In yet another embodiment, the neck portion of the connecting rod may be narrower than the elongate rounded section of the connecting rod. The radius of elongate rounded section of the connecting rod may be smaller than the radius of the leading end portion of the slot. The pair of walls of the head portion of the bone screw may include internal threads. In addition, the shank of the bone screw may include threads. The head portion and the shank of the bone screw may be monolithically formed. The bone screw may be made of titanium or titanium alloy.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein:

FIG. 1 is a side view of a spinal stabilization system in accordance with an embodiment of the present disclosure;

FIG. 2 is a front view of the spinal stabilization system of FIG. 1;

FIG. 4 is a perspective view of a connecting rod of the spinal stabilization system of FIG. 1;

FIG. 5 is a front view of the connecting rod of FIG. 4;

FIG. 6 is a top view of the connecting rod of FIG. 4;

FIG. 7 is a side view of the connecting rod of FIG. 4;

FIG. 8 is a side view of a rod bender device for use with the spinal stabilization system of FIG. 1;

FIG. 9 is a side cross-sectional view of the area of detail indicated in FIG. 8;

DETAILED DESCRIPTION OF EMBODIMENTS

Figure 3:
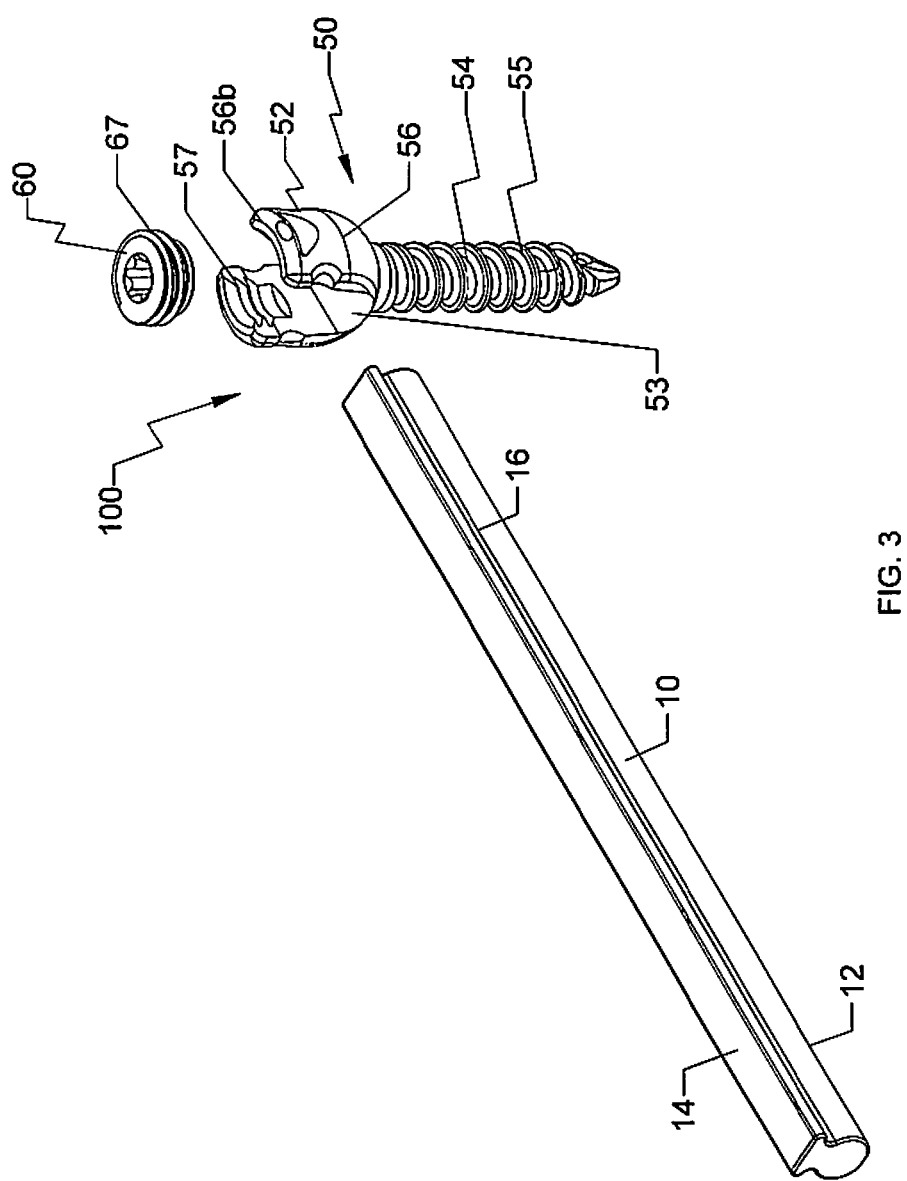
FIG. 3 is an exploded perspective view of the spinal stabilization system of FIG. 1 with parts separated.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIGS. 1-3, an embodiment of the present disclosure is shown generally as a spinal stabilization system 100. Spinal stabilization system 100 includes at least one bone screw 50 defining a longitudinal axis "X-X" (FIG. 2) and a connecting rod 10 defining a longitudinal axis "Y-Y" (FIG. 2). Connecting rod 10 is configured and dimensioned to be selectively and releasably secured to bone screw 50. Connecting rod 10 is defined by an elongate body of a particular length. The elongate body is made of a biocompatible material such as Titanium (Ti—CP) and its alloys (e.g., Ti-6Al-4V), Cobalt-Chrome Alloy (CoCr), or Stainless Steel (SS).

With reference to FIGS. 4 and 5, the elongate body of connecting rod 10 includes an elongate rounded section 12 having a substantially circular cross-section, an elongate head portion 14, and a neck portion 16 that connects and transitions elongate rounded section 12 into elongate head portion 14, thereby providing reduced stress concentration along the elongate body of connecting rod 10. Neck portion 16 may define a pair of concave sides joining elongate head portion 14 to elongate rounded section 12. The elongate body of connecting rod 10 may be monolithically formed as a unitary construct. For example, connecting rod 10 may be machined from a single piece of bar stock.

With particular reference to FIG. 5, elongate head portion 14 has a non-circular cross-section. As shown, elongate head portion 14 has a substantially rectangular cross-section having suitable dimensions of, for example, about 6 mm× about 1 mm (0.246 in.×0.039 in.). However, it is envisioned that elongate head portion 14 may have a cross-section that is substantially square, elliptical or any other shape to add rigidity to rounded section 12 of connecting rod 10.

With reference back to FIGS. 2 and 3, elongate rounded section 12 of connecting rod 10 is configured and dimensioned to be received in a slot 53 defined in a head portion 52 of bone screw 50, as will be described in detail hereinbelow. While elongate head portion 14 of connector rod 10 is disposed above elongate rounded section 12, elongate head portion 14 does not appreciably increase the height profile of the screw-rod combination. Connecting rod 10 affords greater strength and rigidity in comparison with ordinary circular rods with comparable dimensions. As such, connecting rod 10 and bone screw 50 construct affords greater rigidity and strength without increased bulk and profile.

With continued reference to FIGS. 2 and 3, bone screw 50 includes a head portion 52 configured to receive connecting rod 10 therein, a shank 54 extending longitudinally from head portion 52, and a set screw 60 threadably coupled to head portion 52 to secure connecting rod 10 in a slot 53 defined in head portion 52. Head portion 52 of bone screw 50 includes a pair of radially opposing walls 56 defining slot 53 therebetween. Radially opposing walls 56 include internal threads 57 configured for engaging external threads of set screw 60. Slot 53 defines a substantially U-shape channel configured and dimensioned to receive connecting rod 10. Slot 53 includes a leading end portion 53a (FIG. 2) and a trailing end portion 53b (FIG. 2). In particular, leading end portion 53a has an arcuate configuration configured to accommodate a circular cross-section of rounded section 12 of connecting rod 10. The arcuate configuration enables pivoting of connecting rod 10 about leading end portion 53a when connecting rod 10 is partially secured therein, i.e., prior to set screw 60 being fully tightened. Trailing end portion 53b of slot 53 defines a substantially planar surface such that set screw 60 threadably inserted in slot 53 is substantially flush with trailing end portions 56b of the respective walls 56 when connecting rod 10 is positioned within slot 53 and secured by set screw 60 therein.

With particular reference to FIG. 2, slot 53 is flared radially outward, i.e., leading end portion 53a of slot 53 has a smaller radius than the radius of trailing end portion 53b. In this manner, slot 53 provides a slight gap 59 between an inner surface of wall 56 and elongate head portion 14 of connecting rod 10. Under such a configuration, when set screw 60 partially locks connecting rod 10 within slot 53, the surgeon may, e.g., pivot connecting rod 10 about leading end portion 53a of slot 53 to place connecting rod 10 in a desired orientation. Tightening of set screw 60 may orient elongate head portion 14 towards a central orientation. As such, the surgeon needs to maintain connecting rod 12 in a desired orientation during tightening of set screw 60 to achieve the desired orientation of connecting rod 12. Specifically, since connecting rod 10 is pivotable within slot 53, connecting rod 10 can be placed in a desired orientation before being fully locked within slot 53 by fully tightening set screw 60, whereby longitudinal axis "Y-Y" of connecting rod 10 defines an acute angle α with longitudinal axis "X-X" defined by bone screw 50. In this manner, head portion 14 is not parallel to trailing end portions 56b of the walls 56. This allows the surgeon the flexibility of adjusting the orientation of the connecting rod 10 for the rod-screw construct where the angular relationship between the connecting rod 10 and a first bone screw 50 may be different from the angular relationship between the connecting rod 10 and a second bone screw 50.

With continued reference to FIGS. 2 and 3, shank 54 includes threads 55 for engagement through vertebral bodies. Bone screw 50 may be made of a biocompatible material such as Titanium (Ti—CP) and its alloys (e.g., Ti-6Al-4V), Cobalt-Chrome Alloy (CoCr) or Stainless Steel (SS). In particular, head portion 52 and shank 54 may be monolithically formed.

With reference now to FIGS. 8-11, spinal stabilization system 100 may further include rod bender devices 80. Each rod bender devices 80 define matching apertures 88 configured to receive and hold at least a portion of connecting rod 10 therein. Rod bender device 80 includes a handle member 82, an elongate body 84 extending distally from handle portion 82, and an engaging portion 86 coupled to elongate body 84. Elongate body 84 is coupled or formed with handle member 82 and engaging portion 86 so as to reduce stress concentration. Handle member 82 may contain scalloped sections to facilitate gripping by the user. Elongate body 84 may have a rectangular cross-section and may define a cavity along the length thereof to reduce the weight of device. Engaging portion 86 defines at least one aperture 88 adapted and dimensioned to receive therethrough connecting rod 10. In particular, inner walls that define aperture 88 are configured to permit insertion of connecting rod 10 through aperture 88 in a single orientation with respect to such aperture.

Figure 10:
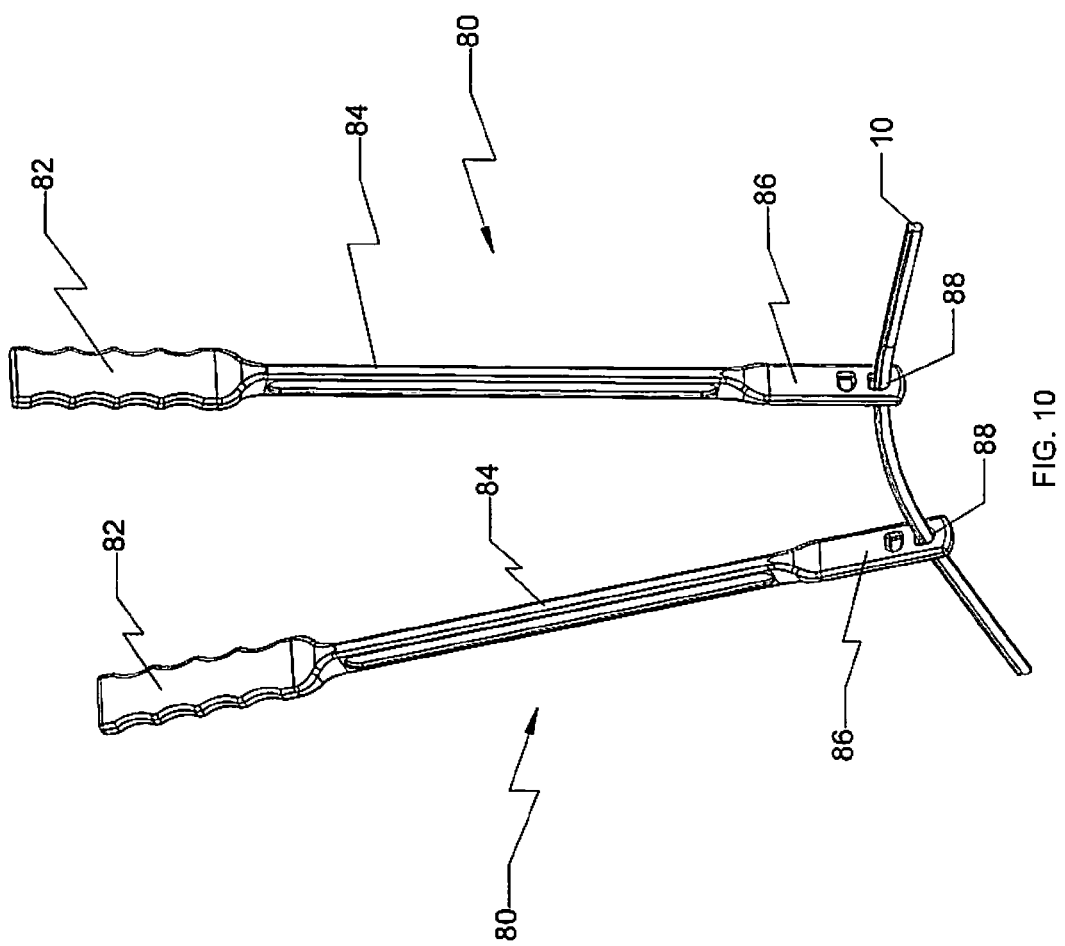
FIG. 10 is a perspective view of a pair of rod bender devices of FIG. 8 having the connecting rod of FIG. 4 inserted therethrough.
Figure 11:
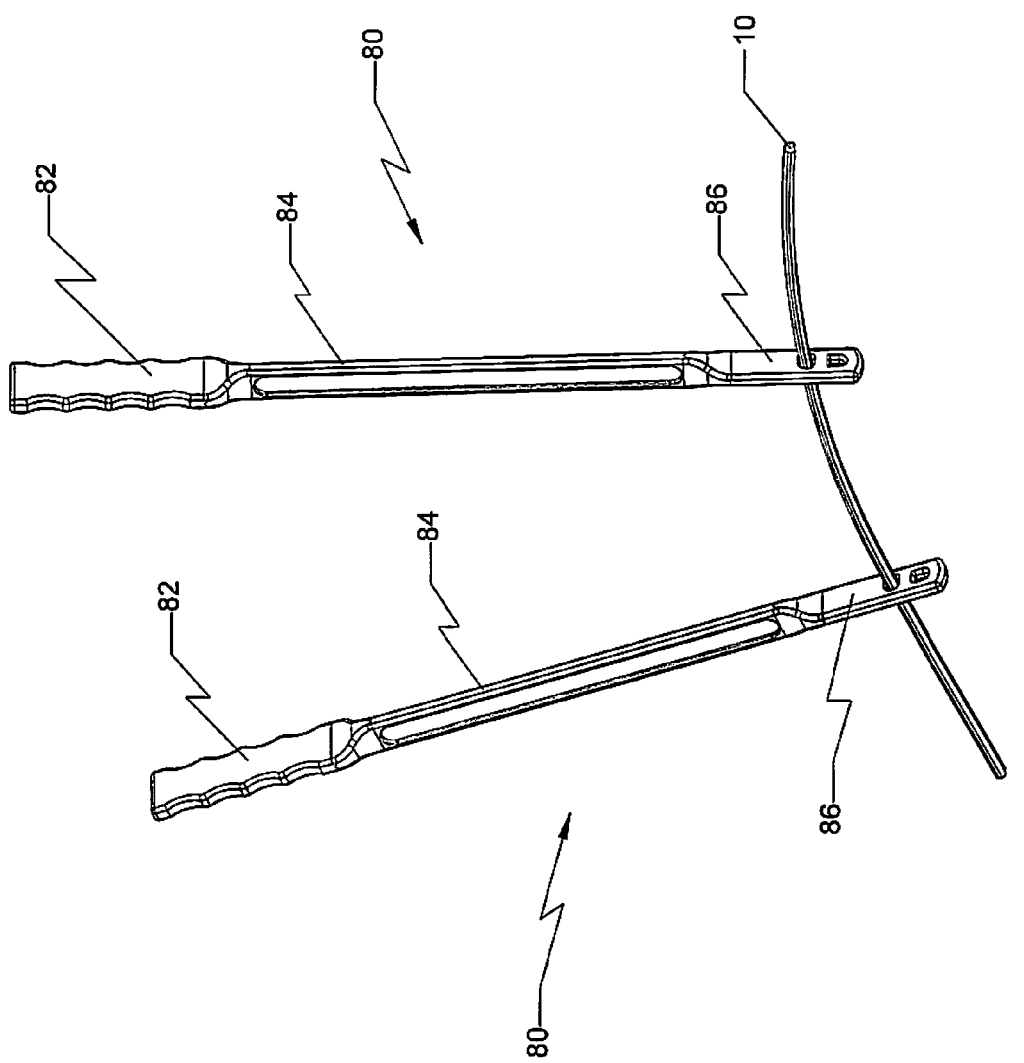
FIG. 11 is a perspective view of the pair of rod bender devices of FIG. 8 having the connecting rod of FIG. 4 inserted therethrough in a different orientation.

With particular reference to FIG. 9, aperture 88 has an arcuate end wall 88a configured to engage elongate rounded section 12 of connecting rod 10, an opposite substantially straight end wall 88b configured to engage the substantially flat portion of elongate head portion 14 of connecting rod 10, and connecting side walls 88c connecting arcuate end wall 88a and the substantially straight end wall 88b. In this manner, connecting rod 10 is inserted into each aperture 88 in a single orientation. Thus, in order to accommodate insertion of connecting rod in aperture 88 in various orientations, a plurality of apertures 88 are defined in engaging portion 86 in different orientations, as shown in FIGS. 10 and 11. For example, the pair of apertures 88 defined in engaging portion 86 is oriented at a 90-degree angle, whereby the rectangular portions of apertures 88 are orthogonal to each other. In this manner, the user can bend connecting rod 10 in both an anterior-posterior orientation and a medial-lateral orientation. It is also contemplated that connecting rod 10 may be inserted in non-corresponding apertures 88 in rod bender devices 80 to facilitate twisting of connecting rod 10, if necessary or desired.

The length of elongate body 84 may be tailored to meet the needs of the surgical application to provide a suitable long moment arm necessary to provide the user a mechanical advantage to bend connecting rod 10. In addition, it is also envisioned that elongate body 84 may be a hollow tubular member and/or define lightening holes to reduce the weight of device 80.

It is also envisioned that spinal stabilization system 100 may be used with other surgical instruments such as, e.g., a rod reduction device, configured to reduce a rod into position in a rod receiving slot in a head of a bone screw with a controlled, measured action. Reference may be made to U.S. Patent Application Publication Nos. 2009-0018593 and 2011-0087298, the entire contents of each of which are incorporated herein by reference, for a detailed discussion of the construction and operation of a rod reduction device.

In use, the user implants a plurality of bone screws 50 in vertebral bodies of a patient. Threaded shank 54 can be driven into the desired vertebral body by providing torsional force via a driving tool (not shown) configured to mate with and grip bone screw 50. After shank 54 is positioned within the vertebral body and the driving tool is removed from bone screw 50, connecting rod 10 is positioned within slot 53 of head portion 52.

In particular, spinal stabilization system 100 can be utilized to correct spinal deformity. Prior to securing connecting rod 10 with bone screw 50, the surgeon can manipulate and correct the curve of the spinal column, i.e., to manually manipulate and reduce the "rib hump." After placing the spine in proper position, the surgeon can bend connecting rod 10 prior to securing connecting rod 10 to the first two points of the spinal column where the construct is to be attached.

The surgeon can bend connecting rod 10 by utilizing the pair of rod bender devices 80. In use, connecting rod 10 is inserted through apertures 88 of rod bender devices 80 and force is applied at handle members 82 of rod bender devices 80, 80 to appropriately contour and shape connecting rod 10 to a desired curve.

At this time, connecting rod 10 is positioned in respective slots 53 of bone screws 50 implanted in vertebral bodies. Set screws 60 can now be threadably inserted into head portion 52 of bone screw 50. Prior to fully securing connecting rod 10 to bone screws 50, the surgeon may once again utilize rod bender devices 80 to position connecting rod 10 to a desired orientation. As discussed hereinabove, slight gap 59 (FIG. 2) between wall 56 and elongate head portion 14 of connecting rod 10 enables the surgeon to pivot connecting rod 10 about leading end portion 53a of slot 53 to position connecting rod 10 to a desired orientation. Upon positioning connecting rod 10 to a desired orientation, the surgeon can now secure connecting rod 10 with bone screws 50 by further tightening set screws 60. The rod and bone screw combination of the present disclosure may provide particular advantages in, e.g., scoliosis or other spinal deformity surgery, in which high stress levels are exerted upon such constructs at particular levels in the construct or over the entire length of such a construct.

Although the illustrative embodiments of the present disclosure have been described herein with reference to the accompanying drawings, the above description, disclosure, and figures should not be construed as limiting, but merely as exemplifications of particular embodiments. It is contemplated that the amount of gap 59 or degree of flare may be tailored to the procedure being performed. For example, surgical procedures that require greater degree of freedom to adjust orientation of connecting rod 10 may utilize a bone screw with a greater degree of flare in slot 53. One skilled in the art will recognize that the present disclosure is not limited to use in spine surgery, and that the instrument and methods can be adapted for use with any suitable surgical device. It is to be understood, therefore, that the disclosure is not limited to those precise embodiments, and that various other changes and modifications may be effected therein by one skilled in the art without departing from the scope or spirit of the disclosure.

What is claimed is:

1. A spinal stabilization system comprising:
   a connecting rod including an elongate rounded section having a circular cross-section, an elongate head portion having a non-circular cross-section, and a neck portion connecting the elongate rounded section with the elongate head portion, the connecting rod being monolithically formed; and
   a bone screw including a head portion defining a slot, a shank extending longitudinally from the head portion, and a set screw configured to secure the connecting rod in the slot, the slot including a leading end portion configured to receive the elongate rounded section of the connecting rod and a trailing end portion configured to threadably engage the set screw, wherein the slot is flared such that elongate rounded section of the connecting rod is pivotable about the leading end portion of the slot.

2. The spinal stabilization system according to claim 1, wherein a radius of the trailing end portion of the slot is larger than a radius of the leading end portion of the slot.

3. The spinal stabilization system according to claim 2, wherein the leading end portion of the slot has an arcuate configuration dimensioned to accommodate the circular cross-section of the elongate rounded section of the connecting rod.

4. The spinal stabilization system according to claim 1, wherein the head portion of the bone screw includes a pair of radially opposing walls defining the slot therebetween, the elongate head portion of the connecting rod movable toward and away from the pair of radially opposing walls of the slot.

5. The spinal stabilization system according to claim 4 wherein the pair of radially opposing walls of the head portion of the bone screw includes internal threads.

6. The spinal stabilization system according to claim 1, wherein the neck portion of the connecting rod is narrower than the elongate rounded section of the connecting rod.

7. The spinal stabilization system according to claim 1, wherein a radius of elongate rounded section of the connecting rod is smaller than a radius of the leading end portion of the slot.

8. The spinal stabilization system according to claim 1, wherein the shank of the bone screw includes threads.

9. The spinal stabilization system according to claim 1, wherein the head portion and the shank of the bone screw are monolithically formed.

10. The spinal stabilization system according to claim 1, wherein the bone screw is made of titanium or titanium alloy.

\* \* \* \* \*